United States Patent [19]
Hippe et al.

[11] Patent Number: 5,510,013
[45] Date of Patent: Apr. 23, 1996

[54] LAYER SYSTEM FOR ELECTROCHEMICAL PROBES

[75] Inventors: Werner Hippe, Gladbeck; Günter Meyer, Essen; Martin Reinke, Dortmund, all of Germany

[73] Assignee: Robert Bosch GmbH, Stuttgart, Germany

[21] Appl. No.: 383,196

[22] Filed: Feb. 3, 1995

Related U.S. Application Data

[63] Continuation of Ser. No. 120,580, Sep. 10, 1993, abandoned.

[51] Int. Cl.$^6$ ............................................. G01N 27/26
[52] U.S. Cl. ................... 204/426; 204/429; 204/424; 204/415; 422/98; 422/82.02; 422/83; 422/94
[58] Field of Search ........................ 204/421, 424, 204/426, 429, 415, 419; 422/98, 82.02, 83, 94

[56] References Cited

U.S. PATENT DOCUMENTS

| | | | |
|---|---|---|---|
| 3,843,400 | 10/1974 | Radford et al. | 204/421 |
| 4,847,783 | 7/1989 | Grace et al. | 422/98 |
| 4,851,105 | 7/1989 | Ishigaro et al. | 204/429 |
| 4,952,904 | 8/1990 | Johnson et al. | 338/36 |
| 5,169,513 | 12/1992 | Mase et al. | 204/429 |
| 5,334,350 | 8/1994 | Friese et al. | 422/98 |

*Primary Examiner*—Bruce F. Bell
*Attorney, Agent, or Firm*—Michael J. Striker

[57] ABSTRACT

A layer system for electrochemical probes has a ceramic substrate, electrodes applied on the ceramic substrate, a sensor layer arranged over the electrodes, and a structure for improving adherence of the sensor layer to the substrate and including at least one adherence improving layer portion which is located under and extends upwardly into the sensor layer and also is sintered with the substrate.

18 Claims, 2 Drawing Sheets

LAYER SYSTEM FOR ELECTROCHEMICAL PROBES

This is a continuation of application Ser. No. 08/120,580 filed Sep. 10, 1993 now abandoned.

BACKGROUND OF THE INVENTION

The present invention relates to a layer system for electrochemical probes.

More particularly, it relates to a layer system with a ceramic substrate in which electrodes are applied and which carries a sensor layer applied over the electrodes and also means for improving adherence of the sensor layer to the substrate.

Layer systems of the above-mentioned general type are known in the art. Such layer systems are utilized, for example, for producing resistance measuring sensors for determination of oxygen content in exhaust gases. In such a system a semi-conductor metal oxide layer with a temperature-dependent or gas concentration-dependent resistance is applied on a ceramic substrate. In addition, the metal oxide layer is covered with a protective layer. The disadvantage of this layer system is that the adherence between the substrate and the metal oxide is relatively poor, since the substrate has a flat and smooth surface. In particular, a probe used in a motor vehicle for determination of the oxygen content in exhaust gases is subjected to extremely high thermal loads. The different thermal expansion coefficients of the substrate and the metal oxide layer lead to the separation of the metal oxide layer from the substrate.

European document EP-A 140 340 discloses a substrate with dispersed ceramic particles which by sintering provide an intimate connection with the substrate. A rough surface is produced by the particles which are firmly connected with the substrate. This method requires that the ceramic particles cover the whole surface and therefore adhere both to the substrate and to the electrode surface. As a result, the contact surface between the sensor layer and the electrodes is reduced. Moreover, the application of the ceramic particles requires a different technology than the thick layer and screen printing technology used for producing the probes.

SUMMARY OF THE INVENTION

Accordingly, it is an object of the present invention to provide a layer system for electrochemical probes, which avoids the disadvantages of the prior art.

In keeping with these objects and with others which will become apparent hereinafter, one feature of the present invention resides, briefly stated, in a layer system for electrochemical probes with a ceramic substrate on which electrodes are applied and which carry a sensor layer applied over the electrodes, which in accordance with the present invention has at least one layer portion which engages in the sensor layer located above, improves the adherence, and is firmly sintered with the substrate.

When the layer system is designed in accordance with the present invention, the production of the adherence improving layer portion is integrated in the screen printing process. Thereby the layer portion is structured itself. The contact surface of the sensor layer with the electrodes remains the same.

In accordance with an especially advantageous feature of the present invention, especially good adherence improvement is obtained when the adherence improving layer portion is formed as a column-shaped anchor. With a column-shaped anchor extending up to over half of the sensor layer, an especially firm clamping of the column-shaped anchor by the sensor layer is produced.

An additional adherence improvement for the electrodes applied on the substrate is obtained when between the electrodes and the metal oxide layer on the one hand, and the substrate on the other hand, an adherence improving layer is provided. This adherence improving layer can be composed, for example, from the same material as the adherence improving layer portion.

Since the layer portion partially extends under an electrode, the adherence improving action of the layer portion is utilized both for the sensor layer and for the electrodes.

The novel features which are considered as characteristic for the invention are set forth in particular in the appended claims. The invention itself, however, both as to its construction and its method of operation, together with additional objects and advantages thereof, will be best understood from the following description of specific embodiments when read in. connection with the accompanying drawings.

DESCRIPTION OF PREFERRED EMBODIMENTS

A layer system for electrochemical probes in accordance with the present invention is described with respect to a resistance measuring sensor for determination of the oxygen content in exhaust gases, as an example.

Figure 1:
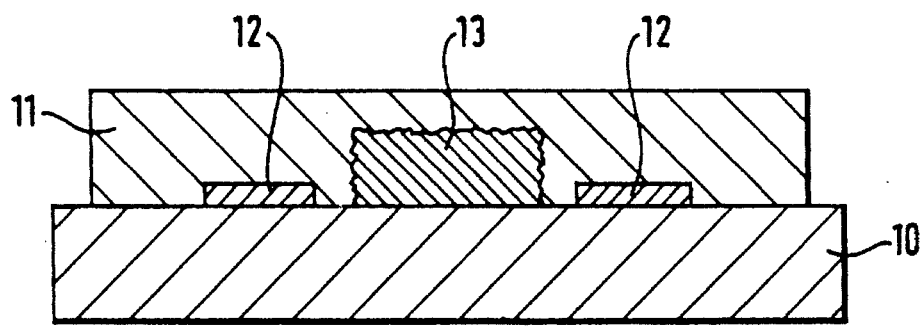
FIG. 1 is a view showing a cross-section of a layer system in accordance with the first embodiment of the present invention.
Figure 3:
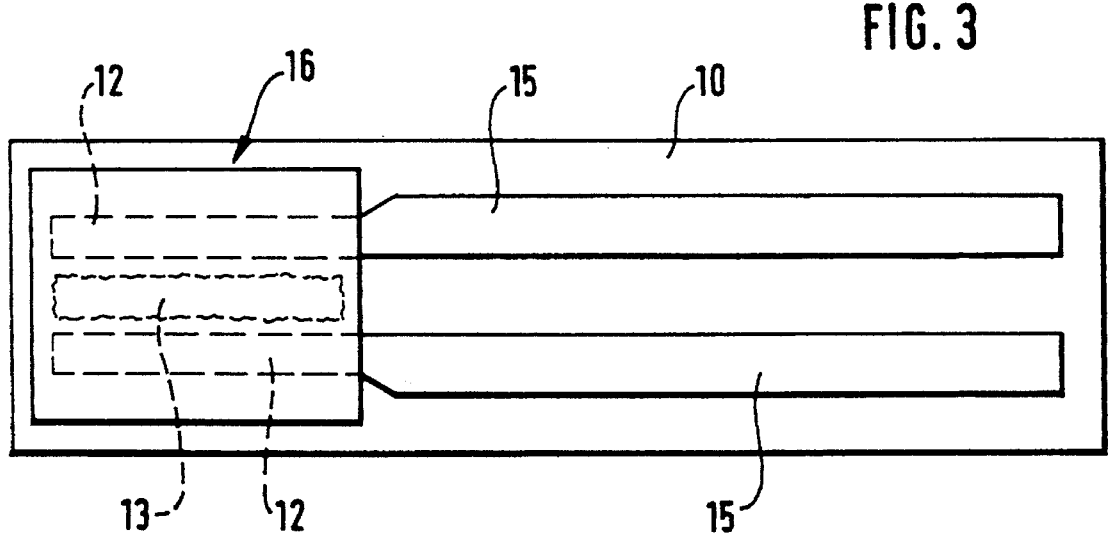
FIG. 3 is a plan view of a probe with a layer system in accordance with the embodiment of FIG. 1.

In accordance with the first embodiment shown in FIG. 1, a substrate 10 is composed of aluminum oxide with more than 90% $Al_2O_3$. The substrate can be used both in pre-sintered and in final-sintered conditions. Two electrodes 12 are arranged on the substrate 10. A sensor layer 11 composed of semi-conductive metal oxide, for example, titanium oxide, is also applied on the substrate 10. The electrodes 12 are imprinted on the substrate 10, for example, by a platinum printing paste composed of 60 vol.-% of platinum and 40 vol.-% of $Al_2O_3$. The sensor layer 11 forms a sensitive region 16 shown in FIG. 3. The electrodes 12 are provided with a conductor path 15 extending outside of the sensitive region 16 to an electrical connection. The resistance measuring sensor is provided conventionally with a heater. The description of such a heater is dispensed with since it has been known for a long time.

An adherence improving layer portion is arranged between the electrodes 12 inside the sensitive region 16. The adherence improving layer portion is formed for example as a column-like anchoring strip 13. The anchoring strip 13, or instead for example one or several anchoring knobs, are imprinted on the substrate 10 by a printing paste, which during sintering forms a rough and/or porous structure. Depending on the thickness of the anchoring strip 13, several layers are printed one after the other. It is advantageous when the column-shaped anchoring strip 13 extends at least over half of (more than half of) the thickness of the sensor layer 11. Moreover, it is advantageous when the anchoring column is located as close as possible to the electrodes 12 and extends along the electrodes.

For forming an adhesion-firm connection between the anchoring strip 13 and the substrate 10 as a base material for the anchoring strip 13, aluminum oxide mixed with a pore-forming material is utilized. Pore-forming materials are known from the prior art for a long time, and therefore are not disclosed in detail. A good adhesive strength of the anchoring strip 13 is obtained when the anchoring strip 13 is composed of the same material as the substrate or at least of a material having similar adhesive properties. Subsequently, the layer system is sintered at a temperature of 1300°–1600° C., for example at 1500° C.

In the next step, the sensitive region 16 is formed. For this purpose the sensor layer 11 is applied over the electrodes 12 and the anchoring strip 13. The sensor layer 11 covers also the front edge of the electrodes 12. Subsequently, the applied sensor layer 11 is sintered at the temperatures of 1000–1350° C. After the sintering, an oxygen permeable protective layer can be applied, for example, by a plasma spraying.

Figure 2:
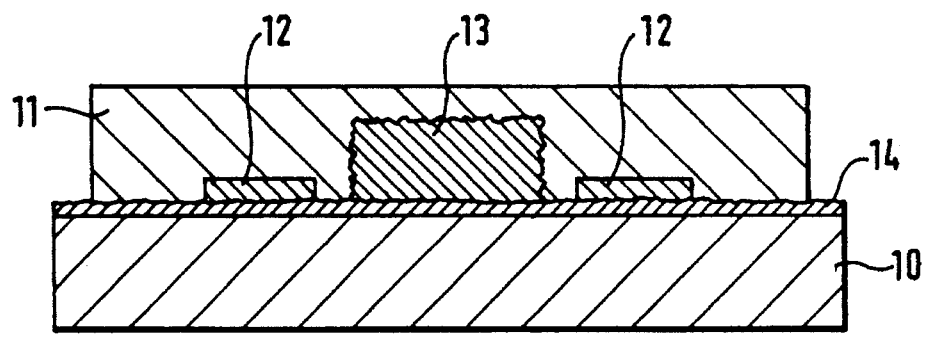
FIG. 2 is a view showing a cross-section of a layer system in accordance with the second embodiment.

The layer system for electrochemical probes in accordance with the second embodiment of the invention is shown in FIG. 2. In this system, an adherence improving intermediate layer 14 is provided additionally to the anchoring strip 13 between the sensor layer and the electrodes 12. The adherence improving intermediate layer 14 is composed for example of aluminum oxide, similarly to the anchoring strip 13. The material of the intermediate layer 14 is preferably selected so that a stepped surface roughness is produced from the substrate 10, the intermediate layer 14, and the anchoring strip 13 whereby an especially good adherence between the layers is provided.

In contrast to the first embodiment, in the first step the adherence improving intermediate layer 14 is applied on the substrate 10 at least in the sensitive region 16 of the measuring sensor. In the next step, both electrodes 12 and the anchoring strip 13 are applied on the adherence improving intermediate layer 14, as in the first embodiment. After the first sintering, the sensitive layer 16 is provided with the sensor layer 11 as in the first embodiment. Subsequently, the sensor layer 11 is sintered as in the first embodiment.

Figure 4:
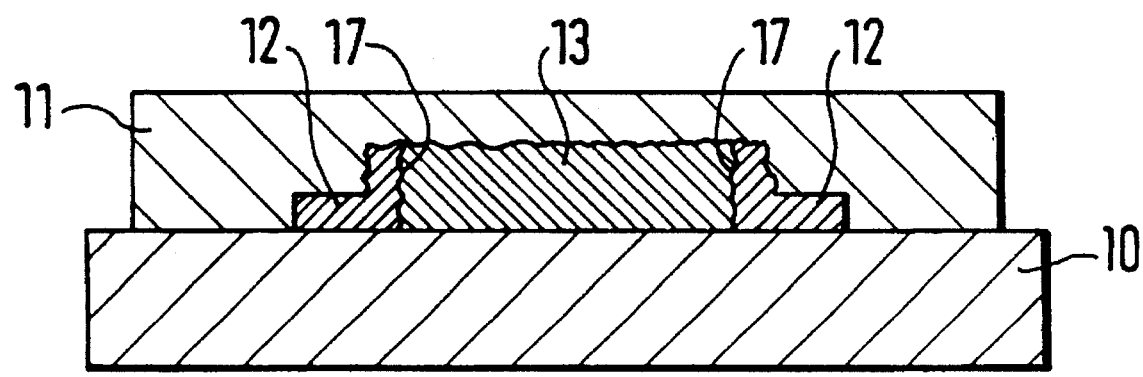
FIG. 4 is a section through a layer system in accordance with a fourth embodiment.

In the third embodiment shown in FIG. 4, in contrast to the preceding embodiments, the layer sequence is selected so that before the application of the electrodes, the column-shaped anchoring strip 13 is imprinted on the substrate. Two flanks 17 extended in the longitudinal direction are formed on the anchoring strip 13. Both electrodes 12 are printed so that correspondingly one part abuts on the respective flank 17 of the anchoring strip 13 and the other part stretches on the substrate 10. The surface roughness of the anchoring strip 13 formed along the flanks 17 is followed by the electrodes 12, and therefore the adherence of the electrodes 12 to the sensor layer 11 is improved. The further steps of production of this probe correspond to the steps of the first embodiment.

It should be mentioned that also a combination of the second and third embodiment is possible. The formation of an adherence improving layer portion is also desirable, in addition to the utilization for resistance measuring sensors, also for solid electrolyte sensors.

It will be understood that each of the elements described above, or two or more together, may also find a useful application in other types of constructions differing from the types described above.

While the invention has been illustrated and described as embodied in a layer system for electrochemical probes, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A layer system for a semi-conductor resistance measuring sensor, comprising a ceramic substrate; electrodes applied on said ceramic substrate; a sensor layer arranged over said electrodes; and means for improving adherence of said sensor layer to said substrate, said means including at least one adherence improving layer portion located under and extending upwardly into said sensor layer, said at least one layer portion extending along at least one of said electrodes and also sintered with said substrate, said at least one layer portion being composed of a material which has at least one layer portion being composed of a same material as said substrate and thereby good adhesive strength is provided between said at least one layer portion and said substrate after sintering of said at least one layer portion and said substrate.

2. A layer system as defined in claim 1, wherein said layer portion is arranged as a strip along at least one of said electrodes.

3. A layer system as defined in claim 1, wherein said layer portion extends partially along at least one of said electrodes.

4. A layer system as defined in claim 1, wherein said layer portion is located between said electrodes.

5. A layer system as defined in claim 1, wherein said layer portion is formed as a column-shaped anchor clamped by said sensor layer.

6. A layer system as defined in claim 5, wherein said sensor layer has a layer thickness, said anchor extending at least over a half of said layer thickness.

7. A layer system as defined in claim 5, wherein said anchor is formed as an anchoring strip.

8. A layer system as defined in claim 1, wherein at least one of said adherence improving layer portion and said sensor layer have a surface which is rough.

9. A layer system as defined in claim 1, wherein said adherence improving layer portion and said sensor layer have surfaces which are rough.

10. A layer system as defined in claim 1, wherein at least one of said adherence improving layer portion and said sensor layer have a porous surface.

11. A layer system as defined in claim 1, wherein said adherence improving layer portion and said sensor layer have porous surfaces.

12. A layer system as defined in claim 1, wherein at least one of said adherence improving layer portion and said sensor layer is composed of a material which has substantially similar properties with a material of said substrate.

13. A layer system as defined in claim 1, wherein at least one of said adherence improving layer portion and said sensor layer is composed of a material of which said substrate is composed.

14. A layer system as defined in claim 1, wherein said adherence improving layer portion and said sensor layer are composed of a material which is at least substantially similar to a material of said substrate.

15. layer system as defined in claim 1, wherein at least one of said adherence improving layer portion and said sensor layer is composed of a material which contains more than 90% $A_2O_3$.

16. A layer system as defined in claim 15, wherein said material is an $Al_2O_3$-containing printing paste with a pore-forming substance which at least during sintering forms a porous surface.

17. A layer system as defined in claim 1, wherein at least one of said adherence improving layer portion and said sensor layer is composed of $Al_2O_3$.

18. A semi-conductor resistance measuring sensor, comprising a ceramic substrate; electrodes applied on said ceramic substrate; a sensor layer arranged over said electrodes; and means for improving adherence of said sensor layer to said substrate, said means including at least one adherence improving layer portion located under and extending upwardly into said sensor layer, said at least one layer portion extending arranged along at least one of said electrodes and also sintered with said substrate, said at least one layer portion being composed of a material which has at least one layer portion being composed of a same material as said substrate and thereby good adhesive strength is provided between said at least one layer portion and said substrate after sintering of said at least one layer portion and said substrate.

* * * * *